United States Patent

Burgess et al.

[11] Patent Number: 5,883,131
[45] Date of Patent: Mar. 16, 1999

[54] CYCLIC SULFONE DERIVATIVES

[75] Inventors: Laurence E. Burgess, Boulder; James P. Rizzi, Niwot, both of Colo.; David J. Rawson, Broadstaris, United Kingdom

[73] Assignee: Pfizer Inc., New York, N.Y.

[21] Appl. No.: 881,092

[22] Filed: Jul. 9, 1997

[51] Int. Cl.⁶ .......................... A61K 31/19; A61K 31/44; C07C 53/02; C07D 211/72
[52] U.S. Cl. .......................... 514/575; 514/347; 562/622; 546/294
[58] Field of Search .............. 562/622; 514/575, 514/347; 546/294

[56] References Cited

U.S. PATENT DOCUMENTS

| | | | |
|---|---|---|---|
| 5,137,914 | 8/1992 | Ohtani et al. | 514/507 |
| 5,506,266 | 4/1996 | Davies et al. | 514/575 |
| 5,646,167 | 7/1997 | MacPherson et al. | 514/357 |
| 5,700,838 | 12/1997 | Dickens et al. | 514/575 |
| 5,703,092 | 12/1997 | Xue et al. | 514/403 |
| 5,712,300 | 1/1998 | Jacobsen | 514/389 |
| 5,753,653 | 5/1998 | Bender et al. | 514/227.5 |
| 5,789,434 | 8/1998 | Kluender et al. | 514/414 |

OTHER PUBLICATIONS

Bender et al, Chem. Abs. No. 127:135724, Sep. 8, 1997.

*Primary Examiner*—Deborah C. Lambkin
*Attorney, Agent, or Firm*—Peter C. Richardson; Paul H. Ginsburg; Jolene W. Appleman

[57] ABSTRACT

A compound of the formula

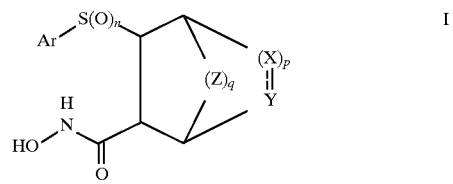

wherein n, p, q, X, Y, Z and Ar are as defined herein, useful in the treatment of arthritis, cancer, tissue ulceration, restenosis, periodontal disease, epidermolysis bullosa, scleritis or other diseases characterized by matrix metalloprotenase activity, as well as AIDS, sepsis, septic shock or other diseases involving the production of TNF.

11 Claims, No Drawings

CYCLIC SULFONE DERIVATIVES

BACKGROUND OF THE INVENTION

The present invention relates to cyclic sulfone derivatives which are inhibitors of matrix metalloproteinases or the production of tumor necrosis factor (TNF) and as such are useful in the treatment of a condition selected from the group consisting of arthritis, cancer, tissue ulceration, restenosis, periodontal disease, epidermolysis bullosa, scleritis and other diseases characterized by matrix metalloproteinase activity, as well as AIDS, sepsis, septic shock and other diseases involving the production of TNF.

This invention also relates to a method of using such compounds in the treatment of the above diseases in mammals, especially humans, and to the pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Friers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62 S11).

SUMMARY OF THE INVENTION

The present invention relates to a compound of the formula

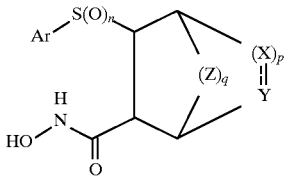

I or a pharmaceutically acceptable salt thereof, wherein the broken line represents an optional double bond;

n is 0, 1 or 2;

p is 0 or 1;

q is 0, 1 or 2;

X, Y and Z are each independently $CR^1R^2$ wherein $R^1$ and $R^2$ are each independently hydrogen, $(C_1-C_6)$alkyl optionally substituted by $(C_1-C_6)$alkylamino, $(C_1-C_6)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_6-C_{10})$aryl$(C_6-C_{10})$aryl, $(C_3-C_6)$cycloalkyl, hydroxy$(C_1-C_6)$alkyl, $(C_1-C_6)$alkyl(hydroxymethylene), piperazinyl, $(C_6-C_{10})$aryl$(C_1-C_6)$alkoxy, $(C_5-C_9)$heteroaryl$(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amino; $(C_2-C_6)$alkenyl, $(C_6-C_{10})$aryl$(C_2-C_6)$alkenyl, $(C_5-C_9)$heteroaryl$(C_2-C_6)$alkenyl, $(C_2-C_6)$alkynyl, $(C_6-C_{10})$aryl$(C_2-C_6)$alkynyl, $(C_5-C_9)$heteroaryl$(C_2-C_6)$alkynyl, $(C_1-C_6)$alkylamino, $(C_1-C_6)$alkylthio, $(C_1-C_6)$alkoxy, trifluoromethyl, $(C_1-C_6)$alkyl (difluoromethylene), $(C_1 C_3)$alkyl (difluoromethylene) $(C_1-C_3)$alkyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_3-C_6)$cycloalkyl, $(C_1-C_6)$alkyl (hydroxymethylene), piperidyl, $(C_1-C_6)$alkylpiperidyl, $(C_1-C_6)$acylamino, $(C_1-C_6)$acylthio, $(C_1-C_6)$acyloxy, $R^3(C_1-C_6)$alkyl wherein $R^3$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl $(C_1-C_6)$alkylpiperazino, $(C_5-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_1-C_6)$alkylpiperidyl$(C_1-C_6)$alkyl, $(C_6-C_{10})$arylpiperidyl$(C_1-C_6)$alkyl, $(C_5-C_9)$heteroarylpiperidyl$(C_1-C_6)$alkyl, $(C_1-C_6)$acylpiperidyl, or a group of the formula

wherein r is 0 to 6;

D is hydroxy, $(C_1-C_6)$alkoxy or $NR^4R^5$ wherein $R^4$ and $R^5$ are each independently selected from the group consisting of hydrogen, $(C_1-C_6)$alkyl optionally substituted by $(C_1-C_6)$alkylpiperidyl, $(C_6-C_{10})$arylpiperidyl, $(C_5-C_9)$heteroarylpiperidyl, $(C_6-C_{10})$aryl, $(C_5-C_9)$heteroaryl, $(C_6-C_{10})$aryl$(C_6-C_{10})$aryl or $(C_3-C_6)$cycloalkyl; piperidyl, $(C_1-C_6)$alkylpiperidyl, $(C_6-C_{10})$arylpiperidyl, $(C_5-C_9)$heteroarylpiperidyl, $(C_1-C_6)$acylpiperidyl, $(C_6-C_{10})$aryl, $(C_5-C_9)$heteroaryl, $(C_6-C_{10})$aryl$(C_6-C_{10})$aryl, $(C_3-C_6)$cycloalkyl, $R^6(C_2-C_6)$alkyl, $(C_1-C_5)$alkyl(CHR$^6$)$(C_1-C_6)$alkyl wherein $R^6$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_1-C_6)$alkyl$)_2$amino, $(C_1-C_6)$acylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino or pyrrolidino; $R^7(C_1-C_6)$alkyl, $(C_1-C_5)$alkyl(CHR$^7$)$(C_1-C_6)$alkyl wherein $R^7$ is piperidyl or $(C_1-C_6)$alkylpiperidyl; and $CH(R^8)COR^9$ wherein $R^8$ is hydrogen, $(C_1-C_6)$alkyl, $(C_6-C_{10})$aryl$(C_1-C_6)$alkyl, $(C_5-C_9)$heteroaryl$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)$alkyl, $R^{10}R^{11}NCO(C_1-C_6)$alkyl or $R^{10}OCO(C_1-C_6)$alkyl wherein $R^{10}$ and $R^{11}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl; and $R^9$ is $R^{12}O$ or $R^{12}R^{13}N$ wherein $R^{12}$ and $R^{13}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl; and Ar is $(C_6-C_{10})$aryl or $(C_5-C_9)$heteroaryl, each of which may be optionally substituted by $(C_6-C_{10})$aryl, $(C_5-C_9)$heteroaryl, $(C_6-C_{10})$aryl$(C_2-C_6)$alkenyl, $(C_5-C_9)$heteroaryl$(C_2-C_6)$alkenyl, $(C_2-C_6)$alkynyl, $(C_6-C_{10})$aryl$(C_2-C_6)$alkynyl or $(C_5-C_9)$heteroaryl$(C_2-C_6)$alkynyl optionally substituted by $(C_1-C_6)$alkyl, $(C_1-C_6)$alkylamino, $(C_1-C_6)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_6-C_{10})$aryl $(C_6-C_{10})$aryl, $(C_3-C_6)$cycloalkyl, hydroxy$(C_1-C_6)$alkyl, $(C_1-C_6)$alkyl(hydroxymethylene), piperazinyl, $(C_6-C_{10})$ aryl($C_1$–$C_6$)alkoxy, ($C_5$–$C_9$)heteroaryl($C_1$–$C_6$)alkoxy, ($C_1$–$C_6$)acylamino, ($C_1$–$C_6$)acylthio, ($C_1$–$C_6$)acyloxy, ($C_1$–$C_6$)alkylsulfinyl, ($C_6$–$C_{10}$)arylsulfinyl, ($C_1$–$C_6$) alkylsulfonyl, ($C_6$–$C_{10}$)arylsulfonyl, amino, ($C_1$–$C_6$) alkylamino, (($C_1$–$C_6$)alkyl)$_2$amino or $R^3$alkyl wherein $R^3$ is defined as above; halo, hydroxy, ($C_1$–$C_6$)alkyl or ($C_1$–$C_6$) alkoxy wherein the alkyl or alkoxy groups may be optionally substituted by ($C_1$–$C_6$)alkylamino, ($C_1$–$C_6$)alkylthio, ($C_1$–$C_6$)alkoxy, trifluoromethyl, ($C_6$–$C_{10}$)aryl, ($C_5$–$C_9$) heteroaryl, ($C_6$–$C_{10}$)arylamino, ($C_6$–$C_{10}$)arylthio, ($C_6$–$C_{10}$) aryloxy, ($C_5$–$C_9$)heteroarylamino, ($C_5$–$C_9$)heteroarylthio, ($C_5$–$C_9$)heteroaryloxy, ($C_6$–$C_{10}$)aryl($C_6$–$C_{10}$)aryl, ($C_3$–$C_6$) cycloalkyl, hydroxy($C_1$–$C_6$)alkyl, ($C_1$–$C_6$)alkyl (hydroxymethylene), piperazinyl, ($C_6$–$C_{10}$)aryl($C_1$–$C_6$) alkoxy, ($C_5$–$C_9$)heteroaryl($C_1$–$C_6$)alkoxy, ($C_1$–$C_6$) acylamino, ($C_1$–$C_6$)acylthio, ($C_1$–$C_6$)acyloxy, ($C_1$–$C_6$) alkylsulfinyl, ($C_6$–$C_{10}$)arylsulfinyl, ($C_1$–$C_6$)alkylsulfonyl, ($C_6$–$C_{10}$)arylsulfonyl, amino, ($C_1$–$C_6$)alkylamino or (($C_1$–$C_6$)alkyl)$_2$amino; ($C_2$–$C_6$)alkenyl, ($C_6$–$C_{10}$)aryl ($C_2$–$C_6$)alkenyl, ($C_5$–$C_9$)heteroaryl($C_2$–$C_6$)alkenyl, ($C_2$–$C_6$) alkynyl, ($C_6$–$C_{10}$)aryl($C_2$–$C_6$)alkynyl, ($C_5$–$C_9$)heteroaryl ($C_2$–$C_6$)alkynyl, ($C_1$–$C_6$)alkylamino, ($C_1$–$C_6$)alkylthio, ($C_1$–$C_6$)alkoxy, trifluoromethyl, ($C_1$–$C_6$)alkyl (difluoromethylene), ($C_1$–$C_3$)alkyl(difluoromethylene) ($C_1$–$C_3$)alkyl, ($C_6$–$C_{10}$)aryl, ($C_5$–$C_9$)heteroaryl, ($C_6$–$C_{10}$) arylamino, ($C_6$–$C_{10}$)arylthio, ($C_6$–$C_{10}$)aryloxy, ($C_5$–$C_9$) heteroarylamino, ($C_5$–$C_9$)heteroarylthio, ($C_5$–$C_9$) heteroaryloxy, ($C_3$–$C_6$)cycloalkyl, ($C_1$–$C_6$)alkyl (hydroxymethylene), piperidyl, ($C_1$–$C_6$)alkylpiperidyl, ($C_1$–$C_6$)acylamino, ($C_1$–$C_6$)acylthio, ($C_1$–$C_6$)acyloxy, $R^3$($C_1$–$C_6$)alkyl or $R^3$($C_1$–$C_6$)alkoxy wherein $R^3$ is ($C_1$–$C_6$)acylpiperazino, ($C_6$–$C_{10}$)arylpiperazino, ($C_5$–$C_9$) heteroarylpiperazino, ($C_1$–$C_6$)alkylpiperazino, ($C_6$–$C_{10}$)aryl ($C_1$–$C_6$)alkylpiperazino, ($C_5$–$C_9$)heteroaryl($C_1$–$C_6$) alkylpiperazino, morpholino, thiomorpholino, piperidino, pyrrolidino, piperidyl, ($C_1$–$C_6$)alkylpiperidyl, ($C_6$–$C_{10}$) arylpiperidyl, ($C_5$–$C_9$)heteroarylpiperidyl, ($C_1$–$C_6$) alkylpiperidyl($C_1$–$C_6$)alkyl, ($C_6$–$C_{10}$)arylpiperidyl($C_1$–$C_6$) alkyl, ($C_5$–$C_9$)heteroarylpiperidyl($C_1$–$C_6$)alkyl, ($C_1$–$C_6$) acylpiperidyl, or a group of the formula

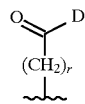

wherein r and D are as defined above;

with the proviso that when q is 1 and X and Y are both $CR^1R^2$ wherein one of either $R^1$ or $R^2$ must be hydrogen, p must be 1;

with the proviso that when q is 0, the compound of formula I is not bicyclic; and with the proviso that when the broken line of formula I represents a double bond, $R^2$ does not exist.

The term "alkyl", as used herein, unless otherwise indicated, includes saturated monovalent hydrocarbon radicals having straight, branched or cyclic moieties or combinations thereof.

The term "alkoxy", as used herein, includes alkyl-O groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents independently selected from the group consisting of fluoro, chloro, cyano, nitro, trifluoromethyl, ($C_1$–$C_6$)alkoxy, ($C_6$–$C_{10}$)aryloxy, trifluoromethoxy, difluoromethoxy and ($C_1$–$C_6$)alkyl.

The term "heteroaryl", as used herein, unless otherwise indicated, includes an organic radical derived from an aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents independently selected from the group consisting of fluoro, chloro, trifluoromethyl, ($C_1$–$C_6$)alkoxy, ($C_6$–$C_{10}$)aryloxy, trifluoromethoxy, difluoromethoxy and ($C_1$–$C_6$)alkyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes acyl-O groups wherein "acyl" is defined above.

Preferred compounds of formula I include those wherein q is 0 or 2.

Other preferred compounds of formula I include those wherein q is 0 or 1.

Other preferred compounds of formula I include those wherein n is 2.

Other preferred compounds of formula I include those wherein X and Y are both $CR^1R^2$ wherein $R^1$ and $R^2$ are hydrogen.

Other preferred compounds of formula I include those wherein Ar is methoxyphenyl, phenoxyphenyl, benzoxyphenyl or halophenyl.

More preferred compounds of formula I include those wherein q is 0, p is 1, m is 2, X and Y are $CR^1R^2$ are hydrogen and Ar is methoxyphenyl, phenoxyphenyl or benzoxyphenyl.

More preferred compounds of formula I include those wherein q is 0, p is 0, m is 2, X and Y are $CR^1R^2$ are hydrogen and Ar is methoxyphenyl, phenoxyphenyl or benzoxyphenyl.

The present invention also relates to a pharmaceutical composition for (a) the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor or (b) the inhibition of matrix metalloproteinases or the production of tumor necrosis factor in a mammal, including a human, comprising an amount of a compound of formula I or a pharmaceutically acceptable salt thereof, effective in such treatments or inhibition and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of formula I or a pharmaceutically acceptable salt thereof.

The present invention also relates to a method for treating a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor (TNF) in a mammal, including a human, comprising administering to said mammal an amount of a compound of formula I or a pharmaceutically acceptable salt thereof, effective in treating such a condition.

DETAILED DESCRIPTION OF THE INVENTION

The following reaction Schemes illustrate the preparation of the compounds of the present invention. Unless otherwise indicated p, q, X, Y, Z and Ar in the reaction Schemes and the discussion that follow are defined as above.

SCHEME 1
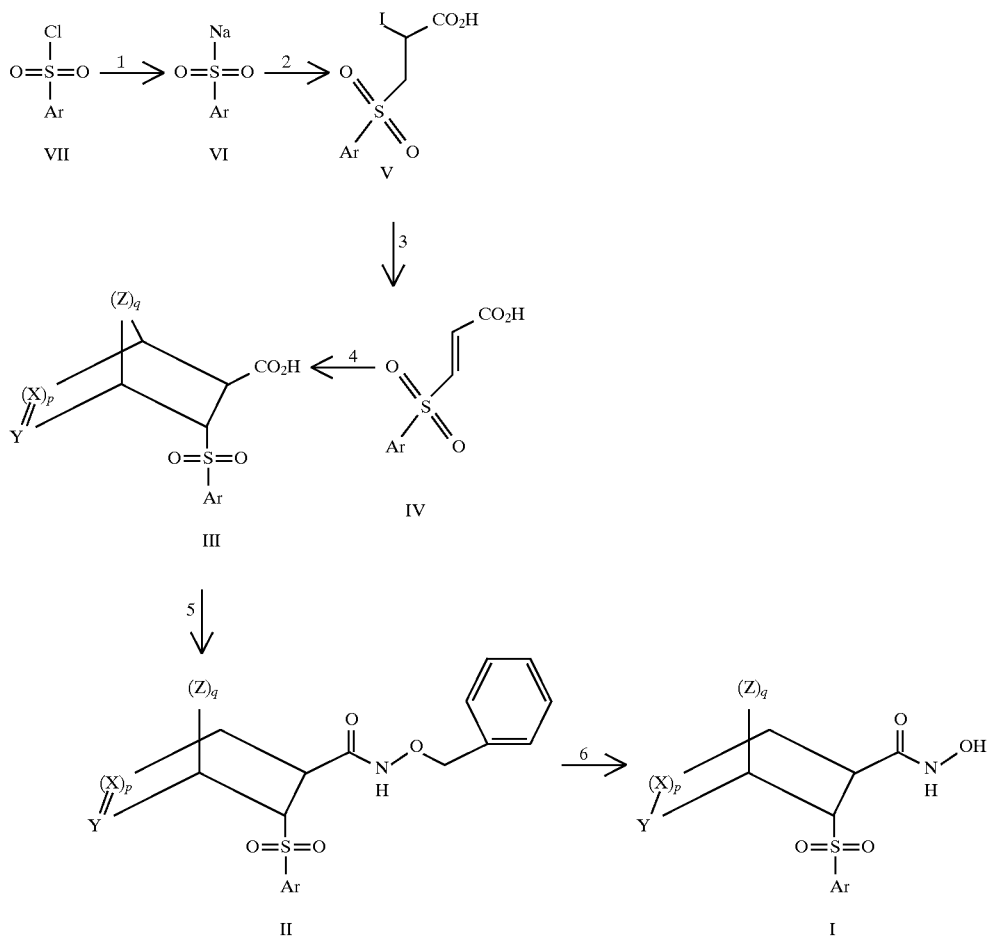
SCHEME 2
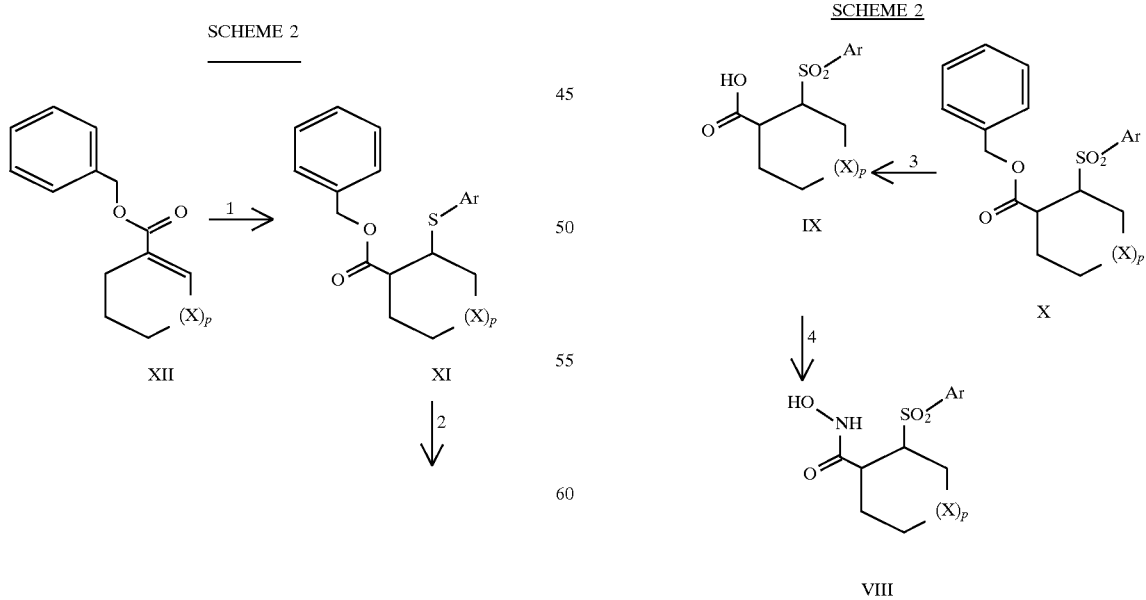

SCHEME 3
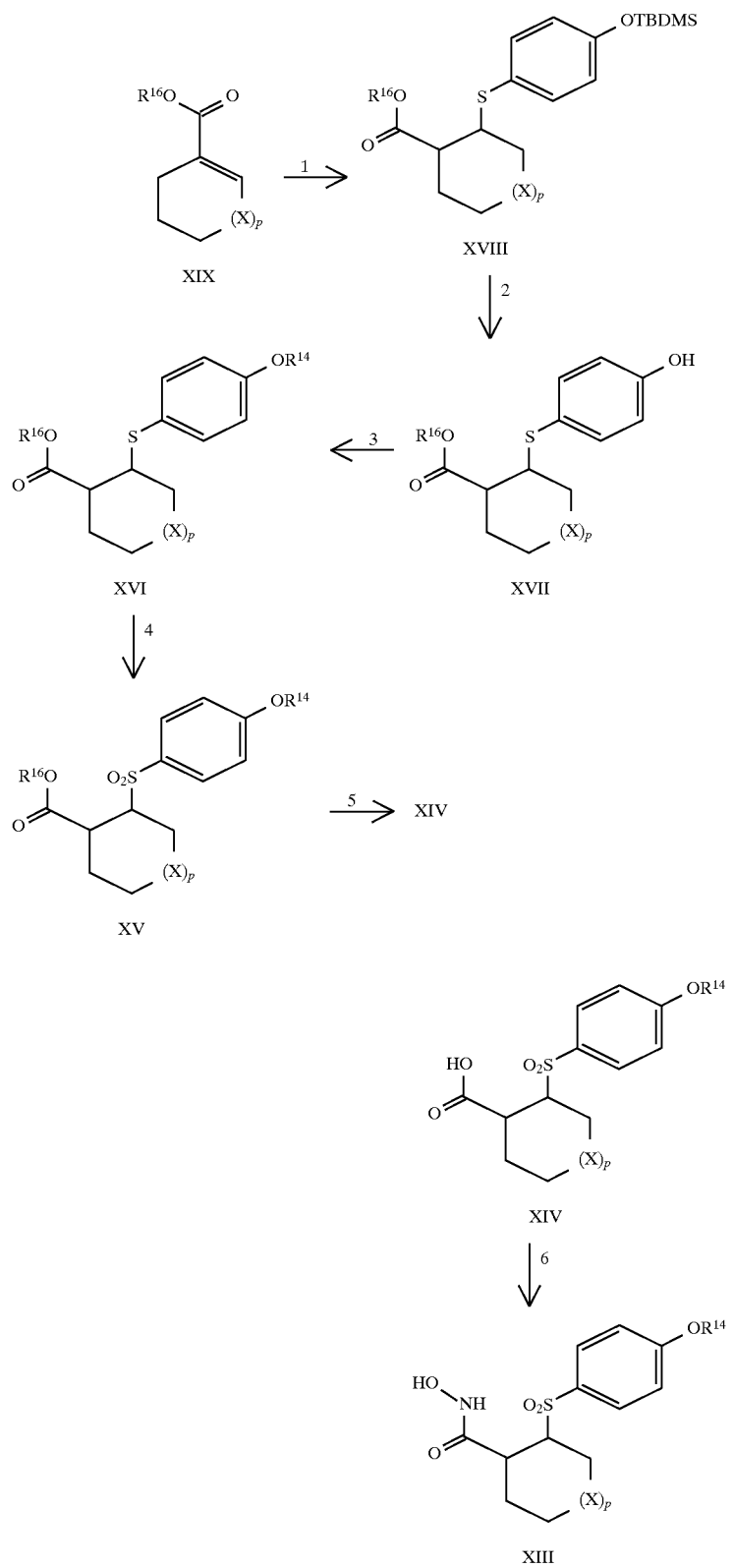

SCHEME 4
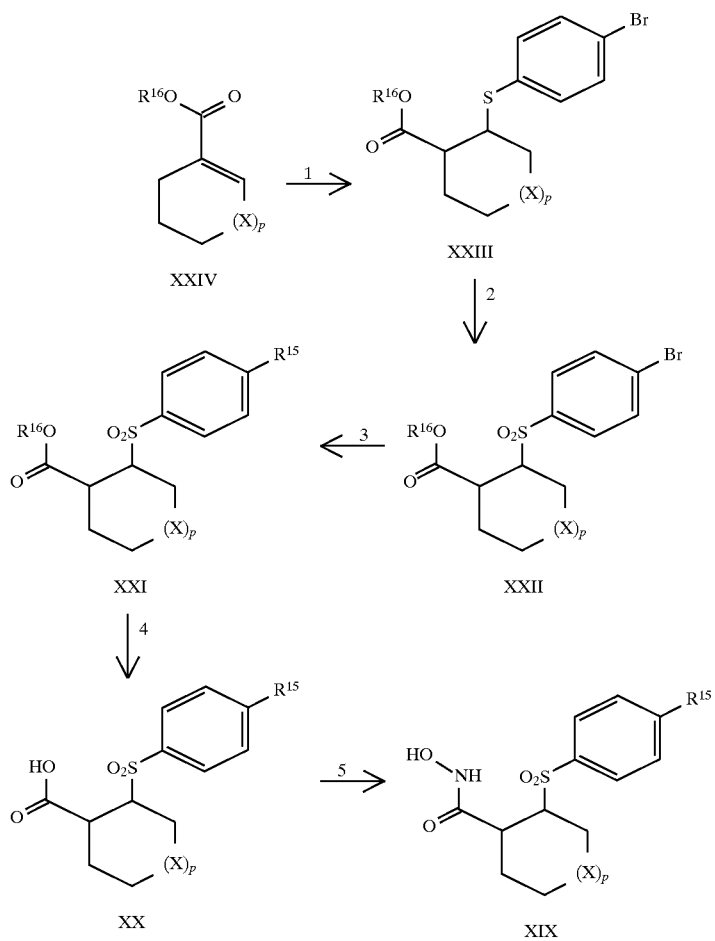
SCHEME 5
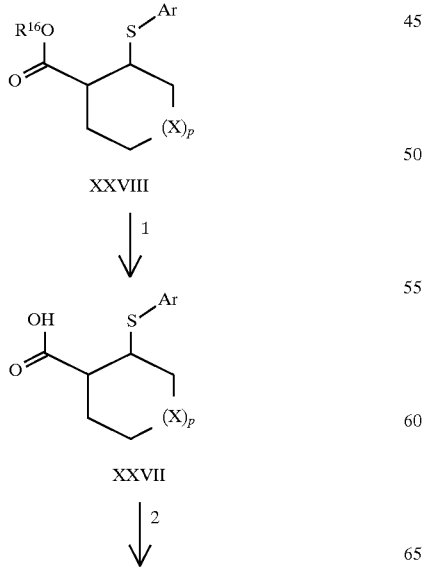
-continued
SCHEME 5
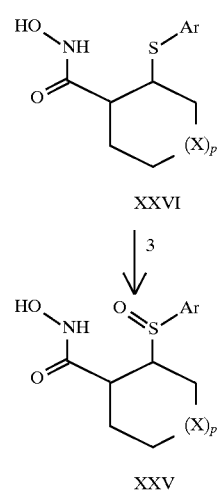
In reaction 1 of Scheme 1, the aryl sulfonyl chloride compound of formula VII is converted to the corresponding sodium aryl sulfinate compound of formula VI by reacting VII with sodium iodine in the presence of a polar aprotic solvent, such as acetone, under inert atmosphere. The reaction mixture is stirred, at room temperature, for a time period between about 12 hours to about 18 hours, preferably about 15 hours.

In reaction 2 of Scheme 1, the compound of formula VI is converted to the corresponding 2-iodo-3-(aryl) sulfonyl propionic acid compound of formula V by reacting VI with acrylic acid and iodine in the presence of a polar aprotic solvent, such as methylene chloride. The reaction mixture is stirred under inert atmosphere, at room temperature, for a time period between about 2.5 days to about 3.5 days, preferably about 3 days.

In reaction 3 of Scheme 1, the compound of formula V is converted to the corresponding (E)-3-(aryl)sulfonyl-prop-2-enoic acid compound of formula IV by treating V with a base, such as triethylamine, under inert atmosphere. The reaction is stirred, at room temperature, for a time period between about 10 hours to about 14 hours, preferably about 12 hours.

In reaction 4 of Scheme 1, the compound of formula IV is converted to the corresponding carboxylic acid compound of formula III by heating IV with an excess amount of a compound of the formula

wherein q is 1 and p is 1, or an excess amount of the diene compound of the formula

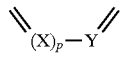

wherein q is 0 and p is 1, to reflux in the presence of a polar aprotic solvent, such as toluene, for a time period between about 40 hours to about 56 hours, preferably about 48 hours.

In reaction 5 of Scheme 1, the compound of formula III is converted to the corresponding N-(benzyloxy)-carboxamide compound of formula III by reacting II with benzylhydroxylaminehydrochloride, dimethylaminopyride and dicyclohexylcarbodiimide in the presence of a polar aprotic solvent, such as methylene chloride, under inert atmosphere. The reaction mixture is stirred, at room temperature, for a time period between about 15 hours to about 25 hours, preferably about 20 hours.

In reaction 6 of Scheme 1, the compound of formula 11 is converted to the corresponding hydroxamic acid compound of formula I by treating II with hydrogen in the presence of a catalyst, such as 5% palladium on barium sulfate, and a polar aprotic solvent, such as methanol. The reaction mixture is stirred for a time period between about 2 hours to about 4 hours, preferably about 3 hours.

In reaction 1 of Scheme 2, the cycloalkenecarboxylate compound of formula XII, wherein p is 0 or 1 and X is $CH_2$, is converted to the corresponding arylthiocycloalkanecarboxylate compound of formula XI by adding a solution of XII in a polar aprotic solvent, such as tetrahydrofuran, to a solution of an arylthio compound of the formula ArSH and a base, such as butyl lithium, in a polar aprotic solvent, such as tetrahydrofuran, under inert atmosphere, at a temperature between about $-75°$ C. to about $-85°$ C., preferable about $-78°$ C. The reaction mixture is allowed to warm to ambient temperature over a time period between about 10 hours to about 14 hours, preferably about 12 hours.

In reaction 2 of Scheme 2, the compound of formula XI is oxidized to the corresponding sulfone compound of formula X by treating XI with a suitable oxidant, such as a catalytic amount of osmium tetraoxide, and a reoxidant, such as N-methylmorpholine oxide, in a polar protic solvent, such as isopropanol. The reaction is carried out in a polar protic solvent, such as isopropanol, for a time period between about 4 hours to about 24 hours, preferably about 12 hours.

In reaction 3 of Scheme 2, the compound of formula X is converted to the corresponding carboxylic acid compound of formula IX by cleaving the ester moiety of X by either hydrolysis using a suitable base, such as sodium hydroxide, in a polar solvent, such as aqueous tetrahydrofuran, or hydrogenolysis using hydrogen in the presence of a polar solvent, such as methanol, and a catalyst, such as 10% palladium on carbon, under a pressure between about 40 psi to about 60 psi, preferably about 50 psi. The reaction is stirred for a time period between about 2 hours to about 12 hours, preferably about 8 hours.

In reaction 4 of Scheme 2, the carboxylic acid compound of formula IX is converted to the corresponding hydroxamic acid compound of formula VIII by treating II with 1-(3-dimethylaminopropyl)-3-ethylcarbodiimide and 1-hydroxybenztriazole in a polar solvent, such as dimethylformamide, followed by the addition of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as N-methylmorpholine. Alternatively, a protected derivative of hydroxylamine or its salt form, where the hydroxyl group is protected as a tert-butyl, benzyl or allyl ether, may be used in the presence of (benzotriazol-1-yloxy)tris(dimethylamino) phosphonium hexafluorphosphate and a base, such as N-methylmorpholine. Removal of the hydroxylamine protecting group is carried out by hydrogenolysis for a benzyl protecting group or treatment with a strong acid, such as trifluoroacetic acid, for a tert-butyl protecting group. The allyl protecting group may be removed by treatment with tributyltinhydride and acetic acid in the presence of catalytic bis(triphenylphosphine) palladium (II) chloride. N,O-bis(4-methoxybenzyl)hydroxylamine may also be used as the protected hydroxylamine derivative where deprotection is achieved using a mixture of methanesulfonic acid and trifluoroacetic acid.

In reaction 1 of Scheme 3, the compound of formula XIX, wherein p is 0 or 1, X is $CH_2$ and $R^{16}$ is a protecting group, such as benzyl, is converted to corresponding compound of formula XVIII, by reacting XIX with a 4-tert-butyidimethylsilylarylthio compound, according to the procedure described above in reaction 1 of Scheme 2.

In reaction 2 of Scheme 3, the compound of formula XVIII is converted to the corresponding compound of formula XVII by the addition of aqueous hydrofluoric acid to a solution of XVIII in a polar aprotic solvent, such as acetonitrile. The reaction mixture is stirred, at room temperature, for a time period between about 2 hours to about 5 hours, preferably about 4 hours.

In reaction 3 of Scheme 3, the compound of formula XVII is converted to the corresponding compound of formula XVI, wherein $R^{14}$ is hydrogen or $(C_1–C_6)$alkyl optionally substituted by $(C_1–C_6)$alkylamino, $(C_1–C_6)$alkylthio, $(C_1–C_6)$alkoxy, trifluoromethyl, $(C_6–C_{10})$aryl, $(C_5–C_9)$heteroaryl, $(C_6–C_{10})$arylamino, $(C_6–C_{10})$arylthio, $(C_6–C_{10})$aryloxy, $(C_5–C_9)$heteroarylamino, $(C_5–C_9)$heteroarylthio, $(C_5–C_9)$heteroaryloxy, $(C_6–C_{10})$aryl$(C_6–C_{10})$aryl, $(C_3–C_6)$cycloalkyl, hydroxy$(C_1–C_6)$alkyl, $(C_1–C_6)$alkyl (hydroxymethylene), piperazinyl, $(C_6–C_{10})$aryl$(C_1–C_6)$ alkoxy, $(C_5-C_9)$heteroaryl$(C_1-C_6)$alkoxy, $(C_1-C_6)$ acylamino, $(C_1-C_6)$acylthio, $(C_1-C_6)$acyloxy, $(C_1-C_6)$ alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amino; or $R^3$alkyl wherein $R^3$ is defined as above, by stirring XVII and suitable primary or secondary alcohol in a polar aprotic solvent, such as tetrahydrofuran, under inert atmosphere. A azidodicarboxylate, such as diethylazidodicarboxylate, and a trialkyl ortriarylphosphine, such as triphenylphosphine, are added and the resulting reaction mixture is stirred for a time period between about 10 hours to about 14 hours, preferably about 12 hours.

In reaction 4 of Scheme 3, the compound of formula XVI is oxidized to the corresponding sulfone compound of formula XV according to the procedure described above in reaction 2 of Scheme 2.

In reaction 5 of Scheme 3, the compound of formula XV is converted to the carboxylic acid compound of formula XIV according to the procedure described in reaction 3 of Scheme 2.

In reaction 6 of Scheme 3, the compound of formula XVI is converted to the corresponding hydroxamic acid compound of formula XIII according to the procedure described above in reaction 4 of Scheme 2.

In reaction 1 of Scheme 4, the compound of formula XXIV, wherein p is 0 or 1, X is $CH_2$ and $R^{16}$ is a protecting group, such as benzyl, is converted to the corresponding compound of formula XXIII by reacting XXIV with a 4-halothiophenol, such as 4-bromothiophenol, according to the procedure described above in reaction 1 of Scheme 2.

In reaction 2 of Scheme 4, the compound of formula XXIII is converted to the corresponding compound of formula XXII according to procedures described above in reacton 4 of Scheme 3.

In reaction 3 of Scheme 4, the compound of formula XXII is converted to the corresponding compound of formula XXI, wherein $R^{15}$ is hydrogen, $(C_6-C_{10})$aryl$(C_2-C_6)$ alkenyl, $(C_5-C_9)$heteroaryl$(C_2-C_6)$alkenyl, $(C_2-C_6)$alkynyl, $(C_6-C_{10})$aryl$(C_2-C_6)$alkynyl, $(C_5-C_9)$heteroaryl$(C_2-C_6)$ alkynyl, $(C_6-C_{10})$aryl or $(C_5-C_9)$heteroaryl optionally substituted by $(C_1-C_6)$alkyl, $(C_1-C_6)$alkylamino, $(C_1-C_6)$ alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$ heteroarylthio, $(C_5-C_9)$heteroaryloxy,$(C_6-C_{10})$aryl$(C_6-C_{10})$ aryl, $(C_3-C_6)$cycloalkyl, hydroxy$(C_1-C_6)$alkyl, $(C_1-C_6)$ alkyl(hydroxymethylene), piperazinyl, $(C_6-C_{10})$aryl$(C_1-C_6)$alkoxy, $(C_5-C_9)$heteroaryl$(C_1-C_6)$alkoxy, $(C_1-C_6)$ acylamino, $(C_1-C_6)$acylthio, $(C_1-C_6)$acyloxy, $(C_1-C_6)$ alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amino; or $R^3$alkyl wherein $R^3$ is defined as above. Coupling partners could be aryl or heteroaryl boronic acids, aryl or heteroaryl stannanes or vinyl compounds.

In reaction 4 of Scheme 4, the compound of formula XXI is converted to the corresponding compound of formula XX according to the procedure described above in reaction 3 of Scheme 2.

In reaction 5 of Scheme 4, the compound of formula XX is converted to the corresponding compound of formula XIX according to the procedure described above in reaction 4 of Scheme 2.

In reaction 1 of Scheme 5, the compound of formula XXVIII, wherein p is 0 or 1, X is $CH_2$ and $R^{16}$ is a protecting group, such as benzyl, is converted to the corresponding compound of formula XXVII according to the procedure described above in reaction 3 of Scheme 2.

In reaction 2 of Scheme 5, the compound of formula XXVII is converted to the corresponding compound of formula XXVI according to the procedure described above in reaction 4 of Scheme 2.

In reaction 3 of Scheme 5, the thioether compound of formula XXVI is oxidized to the corresponding sulfoxide compound of formula XXV using a suitable oxidising agent, such as m-chloroperbenzoic acid, in a polar aprotic solvent, such as dichloromethane, at a temperature between about $-10°$ C. to about $10°$ C., preferably about $0°$ C., for a period of time between about 30 minutes to about 4 hours, preferably about 2 hours.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium slats, such as ammonium, trimethylammonium, diethylammonium, and tris-(hydroxymethyl)-methylammonium slats.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The ability of the compounds of formula I or their pharmaceutically acceptable salts (hereinafter also referred to as the compounds of the present invention) to inhibit matrix metalloproteinases or the production of tumor necrosis factor (TNF) and, consequently, demonstrate their effectiveness for treating diseases characterized by matrix metalloproteinase or the production of tumor necrosis factor is shown by the following in vitro assay tests.

Biological Assay

Inhibition of Human Collagenase (MMP-1)

Human recombinant collagenase is activated with trypsin using the following ratio: 10 $\mu$g trypsin per 100 $\mu$g of collagenase. The trypsin and collagenase are incubated at room temperature for 10 minutes then a five fold excess (50 $\mu$g/10 $\mu$g trypsin) of soybean trypsin inhibitor is added.

10 mM stock solutions of inhibitors are made up in dimethyl sulfoxide and then diluted using the following Scheme:

10 mM→120 $\mu$M→12 $\mu$M→1.2 $\mu$M→0.12 $\mu$M

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25$\mu$l is then added to appropriate wells of the microfluor plate. Final concentration of collagenase in the assay is 100 ng/ml.

Substrate (DNP-Pro-Cha-Gly-Cys(Me)-His-Ala-Lys (NMA)-$NH_2$) is made as a 5 mM stock in dimethyl sulfoxide and then diluted to 20 $\mu$M in assay buffer. The assay is initiated by the addition of 50$\mu$l substrate per well of the microfluor plate to give a final concentration of 10 $\mu$M.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone x 100). $IC_{50}$'s are determined from the concentration of inhibitor that gives a signal that is 50% of the control.

If $IC_{50}$'s are reported to be <0.03 µM then the inhibitors are assayed at concentrations of 0.3 µM, 0.03 µM, 0.03 µM and 0.003 µM.

Inhibition of Gelatinase (MMP-2)

Inhibition of gelatinase activity is assayed using the Dnp-Pro-Cha-Gly-Cys (Me)-His-Ala-Lys(NMA)-$NH_2$ substrate (10 µM) under the same conditions as inhibition of human collagenase (MMP-1).

72kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 µM, 3 µM, 0.3 µM and 0.03 µM. Each concentration is done in triplicate.

Fluorescence readings (360 nm excitation, 460 emission) are taken at time zero and then at 20 minutes intervals for 4 hours.

$IC_{50}$'s are determined as per inhibition of human collagenase (MMP-1). If $IC_0$'s are reported to be less than 0.03 µM, then the inhibitors are assayed at final concentrations of 0.3 µM, 0.03 µM, 0.003 µM and 0.003 µM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[$CH_2CH(CH_3)_2$]CO-Leu-Gly-$OC_2H_5$] yields a mercaptan fragment that can be monitored in the presence of Ellman's reagent.

Human recombinant prostromelysin is activated with trypsin using a ratio of 1 µl of a 10 mg/ml trypsin stock per 26 µg of stromelysin. The trypsin and stromelysin are incubated at 37° C. for 15 minutes followed by 10 µl of 10 mg/ml soybean trypsin inhibitor for 10 minutes at 37° C. for 10 minutes 37° C. to quench trypsin activity.

Assays are conducted in a total volume of 250 µl of assay buffer (200 mM sodium chloride, 50 mM MES, and 10 mM calcium chloride, pH 6.0) in 96-well microliter plates. Activated stromelysin is diluted in assay buffer to 25 µg/ml. Ellman's reagent (3–Carboxy-4-nitrophenyl disulfide) is made as a 1 M stock in dimethyl formamide and diluted to 5 mM in assay buffer with 50 µl per well yielding at 1 mM final concentration.

10 mM stock solutions of inhibitors are made in dimethyl sulfoxide and diluted serially in assay buffer such that addition of 50 µL to the appropriate wells yields final concentrations of 3 µM, 0.3 µM, 0.003 µM, and 0.0003 µM. All conditions are completed in triplicate.

A 300 mM dimethyl sulfoxide stock solution of the peptide substrate is diluted to 15 mM in assay buffer and the assay is initiated by addition of 50 µl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 µM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 µM, 3 µM, 0.3 µM, and 0.03 µM.

Substrate (Dnp-Pro-Cha-Gly-Cys(Me)-His-Ala-Lys (NMA)-$NH_2$) is prepared as for inhibition of human collagenase (MMP-1) and 50 µl is added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 µM, inhibitors are then assayed at final concentrations of 0.3 µM, 0.03 µM, 0.003 µM and 0.0003 µM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of 2 $\times 10^6$/ml in HBSS containing 1% BSA. Differential counts determined using the Abbott Cell Dyn 3500 analyzer indicated that monocytes ranged from 17 to 24% of the total cells in these preparations.

180µl of the cell suspension was aliquoted into flate bottom 96 well plates (Costar). Additions of compounds and LPS (100 ng/ml final concentration) gave a final volume of 200 µl. All conditions were performed in triplicate. After a four hour incubation at 37° C in an humidified $CO_2$ incubator, plates were removed and centrifuged (10 minutes at approximately 250×g) and the supernatants removed and assayed for TNFα using the R&D ELISA Kit.

For administration to humans for the inhibition of matrix metalloproteinases or the production of tumor necrosis factor, a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is possible to administer the compounds of the present invention topically, e.g., when treating inflammatory conditions of the skin and this may be done by way of creams, jellies, gels, pastes, and ointments, in accordance with standard pharmaceutical practice.

The present invention is illustrated by the following examples, but is not limited to the details thereof.

EXAMPLE 1

N-Hydroxy-3-(4-phenoxy-benzenesulfonvl)-bicyclo [2.2.2]octane-2-carboxamide

A mixture of 0-benzyl hydroxamate (0.17 grams; 0.36 mmol) and 5% palladium or barium sulfate (0.30 grams) in methanol (50 mL) was placed under an atmosphere of hydrogen (40 psi) and shaken vigorously for 3 hours. The reaction mixture was then filtered and concentrated in vacuo to provide a glassy solid (0.15g). Purification via flash chromatography (30:70:2.5:0.5 of ethyl acetate:hexanes:acetic acid:methanol) on silica gel produced the pure hydroxamic acid as an off-white foamy solid (96 mg; 60%). M.P. 89.9°–91.8° C.; $^1$H NMR (250 MHz, D$_4$—MeOH) δ7.80 (d, 2H, J=8.6 Hz), 7.43 (t, 2H, J=7.6 Hz), 7.23 (t, 1H, J=7.3 Hz), 7.11 (t, 4H, J=9.1 Hz), 3.88 (d, 1H, J=7.7 Hz), 2.84 (d, 1H, J=7.2 Hz), 2.18 (br s, 2H), 1.80–1.40 (m, 4H); $^{13}$C NMR (75.5 MHz, D$_4$—MeOH) δ21.5, 25.9, 26.6, 27.4, 32.3, 42.4, 63.6, 118.8, 121.5, 126.2, 131.3, 132.0, 133.1, 156.6, 164.1, 171.8; IR (drifts): 3303–3230, 2943, 2870, 1665, 1582, 1488, 1247, 1143 cm$^{-1}$. HRMS: calculated for $C_{21}H_{24}NO_5$ 402.1375; Found 402.1352.

EXAMPLE 2

3-(4-phenoxy-benzenesulfonyl)-bicyclo[2.2.2]oct-5-ene-2-carboxvlic acid

A stirred solution of vinyl sulfone-carboxylate (0.34 grams; 1.1 mmol) and 1,3-cyclohexadiene (5 mL, excess) in dry toluene (10 mL) was heated to reflux (120° C.) for 48 hours. The reaction was concentrated in vacuo to give a blue-green oil (0.73 grams) which was purified via flash chromatography (20% ethyl acetate, 2% acetic acid, 2% methanol in hexanes on silica gel) to give the bicyclic sulfone as a light yellow oil (0.24 grams; 56%). Major Diastereomer: $^1$H NMR (250 MHz, CDCl$_3$) δ7.85–7.74 (m, 2H), 7.44–7.37 (m, 2H), 7.22 (c, 1H), 7.10–7.01 (m, 4H), 6.30 (t, 1H, J=6.9 Hz), 6.11 (t, 1H, J=6.9 Hz), 3.13 (d, 1H, J=4.9 Hz), 2.89 (dd, 1H, J=5.8, 2.1 Hz), 2.63–2.57 (m, 2H), 1.90–1.16 (m, 4H). LRMS: 385 (M+1), 402 (M+18).

EXAMPLE 3

N-Hydroxy-2-(4-methoxybenzenesulfonyl)-cyclohexane-1-carboxamide

N-Butyl lithium (0.56 ml of a 2.5M solution in hexanes) was added to a stirred solution of 4-methoxythiophenol (1.94 grams. 13.9 mmol) in tetrahydrofuran (40 ml) at −78° C. under a nitrogen atmosphere. After 1 hour a solution of benzyl 1-cyclohexene-1-carboxylate (6 grams, 27.8 mmol) in tetrahydrofuran (5 ml) was added by cannula and the reaction mixture was allowed to warm to room temperature over 12 hours. The reaction was quenched with saturated sodium chloride solution and diluted with ethyl acetate. The organic layer was separated, dried over sodium sulfate and concentrated. The crude mixture was purified by silica gel chromatography (elution with 98% hexane/2% ethyl acetate) to provide benzyl-2-(4-methoxybenzenothio)-1-cyclohexane-1-carboxylate.

Osmium tetroxide (1.85 ml of a 2.5% solution in 2-methyl-2-propanol) was added to a stirred solution of benzyl-2-(4-methoxybenzenethio)-1-cyclohexane-1-carboxylate (3.3 grams, 9.27 mmol) and 4-methylmorpholine N-oxide (2.71 grams, 23.2 mmol) in aqueous acetone (40 ml water/80 ml acetone) at room temperature. After 2 hours the solvent was removed in vacuo and the residue was partitioned between dilute hydrochloric acid an dethyl acetate. The ethyl acetate layer was washed with brine, dried (sodium sulfate) and concentrated. The crude mixture was purified by silica gel chromatography (elution with 90% hexane/10% ethyl acetate) to provide benzyl-2-(4-methoxybenzenesulfonyl)-1-cyclohexane-1-carboxylate.

Benzyl-2-(4-methoxybenzenesulfonyl)-1-cyclohexane-1-carboxylate (3.1 grams, 8.0 mmol) was dissolved in 300 ml ethyl alcohol. 10% Palladium on carbon (0.3 grams) was added and the reaction mixture was heated at 60° C. under a pressure of 50psi hydrogen for 12 hours. The mixture was cooled, the catalyst removed by filtration and the solvent concentrated. The crude mixture was purified by silica gel chromatography (elution with 95% dichloromethane/5% methanol) to provide 2-(4-methoxybenzenethio)-1-cyclohexane-1-carboxylate.

1-Hydroxybenztriazole (0.49 grams, 3.6 mmol) and 1-(3-dimethylaminopropyl)-3-ethylcarbodiimide (0.69 grams, 3.6 mmol) were added to a stirred solution of 2-(4-methoxybenzenesulfonl)-1-cyclohexane-1-carboxylate (0.9 grams, 3.0 mmol) in dimethylformamide (20 ml) at room temperature. After 30 minutes hydroxylamine hydrochloride (0.83 grams, 12.0 mmol) and triethylamine (1.83 grams, 18.1 mmol) were added and the mixture was stirred for 12 hours. The reaction mixture was diluted with ethyl acetate and washed with sodium bicarbonate solution. The organic layer was washed with 2M hydrochloric acid, then brine and dried (sodium sulfate) before concentrating. The product was purified by recrystallization (ethyl acetate/methanol) to give N-hydroxy-2-(4-methoxybenzenesulfonyl)-cyclohexane-1-carboxamide as a crystalline solid. The relative stereochemistry of the two substituents at the ring junction was shown to be cis by X-ray crystallography. Mass spectrum (thermospray): m/Z 331.1 ($MNH_4^+$). $^1H$ NMR ($CDCl_3$, 400 MHz, ppm) δ9.00 (s, 1H), 7.80 (d, 2H), 7.05 (d, 1H), 3.90 (s,3H), 3.15 (dt, 1H), 3.10 (m, 1H), 2.20–1.85 (m, 4H), 1.80–1.20 (m, 6H). Analysis found: C,53.69; H, 6.15; N, 4.37. $C_{14}H_{19}NSO_5$ requires C,53.66; H, 6.11; N, 4.47.

EXAMPLE 4

N-Hydroxy-2-(4-(2-N-phthalimido)ethoxy-benzenesulfonyl)-cyclohexane-1-carboxamide N-Butyl lithium (1.5 ml a 2.5M solution in hexanes) was added to a stirred solution of 4-t-butyldimethylsilyloxthiophenol (14.8 grams, 61.7 mmol) in tetrahydrofuran (300 ml) at −78° C. under a nitrogen atmosphere. After 1 hour a solution of benzyl 1-cyclohexene-1-carboxylate (8 grams, 37 mmol) in tetrahydrofuran (15 ml) was added by cannula and the reaction mixture was allowed to warm to room temperature over 12 hours. The reaction was quenched with saturated sodium chloride solution and diluted with ethyl acetate. The organic layer was separated, dried (sodium sulfate) and concentrated. The crude mixture was purified by silica gel chromatography (elution with 98% hexane/2% ethyl acetate) to provide benzyl-2-(4-t-butyldimethylsilyloxybenzenethio)-1-cyclohexane-1-carboxylate.

Hydrofluoric acid (5 ml of a 40% aqueous solution) was added to a stirred solution ofbenzyl-2-(4-t-butyidimethylsilyloxybenzenothio)-1-cyclohexane-1-carboxylate (5 grams, 11.3 mmol) in acetonitrole (50 ml) at room temperature. After 12 hours the reaction mixture was poured into aqueous ammonium chloride and extracted with dichloromethane. The organics were dried (sodium sulfate) and concentrated. The crude mixture was purified by silica gel chromatography (elution with 97% dichloromethane/3% methanol) to provide benzyl-2-(4-hydroxybenzenethio)-1-cyclohexane-1-carboxylate.

Benzyl-2-(4-hydroxybenzenethio)-1-cyclohexane-1-carboxylate (1 gram, 2.92 mmol) and N-(2-hydroxyethyl) phthalimide (0.56 grams, 292 mmol) were dissolved in tetrahydrofuran (30 ml) and stirred at 0° C. under a nitrogen atmosphere. Triphenylphosphine (0.84 grams, 3.22 mmol) and diethylazidodicarboxylate (0.61 grams, 3.51 mmol) were then added and the solution was stirred for 12 hours at 50° C. The mixture was concentrated and the residue partitioned between ethyl acetate and water. The organic layer was dried (sodium sulfate) and concentrated. The crude mixture was purified by silica gel chromatography (elution with 99% dichloromethane/1% methanol) to provide benzyl-2-(4-(2-N-phthalimido)ethoxy-benzenethio)-1-cyclohexane-1-carboxylate.

Osmium tetroxide (0.38 ml of a 2.5% solution in 2-methyl-2-propanol) was added to a stirred solution of benzyl-2-(4–2-N-phthalimido)ethoxy-benzenethio)-1-cyclohexane-1-carboxylate (0.98 grams, 1.91 mmol) and 4-methylmorpholine N-oxide (0.56 grams, 4.77 mmol) in aqueous acetone (7 ml water/14 ml acetone) at room temperature. After 12 hours the solvent was removed in vacuo and the residue was partitioned between dilute hydrochloric acid and ethyl acetate. The ethyl acetate layer was washed with brine, dried (sodium sulfate) and concentrated. The crude mixture was purified by silica gel chromatography (elution with 99% dichloromethane/1% methanol) to provide benzyl-2-(4-(2-N-phthalimido)ethoxy-benzenesulfonyl)-1-cyclohexane-1-carboxylate.

Benzyl-2-(4-(2-N-phthalimido)ethoxy-benzenesulfonyl)-1-cyclohexane-1-carboxylate (0.54 grams, 1.0 mmol) was dissolved in 60 ml ethyl alcohol. 1 0% Palladium on carbon (60 mg) was added and the reaction mixture was heated at 60° C. under a pressure of 50 psi hydrogen for 12 hours. The mixture was cooled, the catalyst removed by filtration and the solvent concentrated. The crude mixture was purified by silica gel chromatography (elution with 98% dichloromethane/2% methanol) to provide 2-(4-(2-N-phthalimido)ethoxy-benzenesulfonyl)-1-cyclohexane-1-carboxylate.

1-Hydroxybenztriazole (78 mg, 0.58 mmol) and 1-(3-dimethylaminopropyl)-3-ethylcarbodiimide (0.11 grams, 0.58 mmol) were added to a stirred solution of 2-(4-(2-N-phthalimido)ethoxy-benzenesulfonyl)-1-cyclohexane-1-carboxylate (0.22 grams, 0.48 mmol) in dimethylformamide (5 ml) at room temperature. After 30 minutes hydroxylamine hydrochloride (0.13 grams, 1.92 mmol) and triethylamine (0.29 grams, 2.89 mmol) were added and the mixture was stirred for 12 hours. The reaction mixture was diluted with ethyl acetate and washed with sodium bicornate solution. The organic layer was washed with 2M hydrochloric acid, then brine and dried (sodium sulfate) before concentrating. The product was purified by silica gel chromatography (elution with 98% dichloromethane/2% methanol) to provide N-hydroxy-2-(4-(2-N-phthalimido)ethoxy-benzenesulfonyl)-cyclohexane-1-carboxamide. Mass spectrum (thermospray): m/Z 473 ($MH^+$). $^1H$ NMR ($CDCl_3$, 400 MHz, ppm) δ7.90–7.80 (m, 4H), 7.75 (d, 2H), 7.10 (d, 2H), 4.40 (t, 2H), 4.10 (t, 2H), 2.80 (m, 1H), 2.40 (dt, 1H), 1.90Δ1.20 (m, 8H). Analysis found: C,57.85; H, 5.30; N, 5.94. $C_{23}H_{24}N_2SO_7 \cdot H_2O$ requires C,57.37; H, 5.23; N, 5.82.

The title compounds of Example 5–6 were prepared by a method analogous to that described in Example 4.

EXAMPLE 5

N-Hydroxy-2-(4-(benzyloxy)benzenesulfonvl)-cyclohexane-1-carboxamide

Mass spectrum (thermospray): m/Z 407.1 ($MNH_4^+$). $^1H$ NMR ($CDCl_3$, 400 MHz, ppm) δ7.80 (d, 2H), 7.50–7.30 (m, 5H), 7.20 (d, 2H), 5.20 (d, 2H), 2.80 (m, 1H), 2.40 (dt, 1 H), 1.90–1.30 (m,8H). Analysis found: C,59.90; H, 5.83; N, 3.08. $C_{20}H_{23}NSO_5 \cdot 0.5H_2O$ requires C,60.28; H, 6.07; N, 3.52.

EXAMPLE 6

N-Hydroxy-2-(4-(4-methoxyphenpropyloxy) benzenesulfonyl)-cyclohexane-1-carboxamide Mass spectrum (thermospray): m/Z 449.2 (MH$^+$). $^1$H NMR (CDCl$_3$, 400 MHz, ppm) δ9.30 (1H, br s), 7.75 (2H, d), 7.10 (d, 2H), 7.00 (d, 2H), 6.85 (d, 2H), 4.60 (d, 1H), 4.00 (t, 2H), 3.85 (m, 1H), 3.80 (s, 3H), 3.10 (dt, 1H), 2.75 (t, 3H), 2.25 (d, 1H), 2.10 (m, 2H), 1.70–1.10 (m, 8H).

EXAMPLE 7

N-Hydroxy-2-(4-(2-methoxy-5-pyridyl)-benzenesulfonyl)-cyclohexane-1-carboxamide

N-Butyl lithium (0.92 ml of a 2.5M solution in hexanes) was added to a stirred solution of 4-bromothiophenol (4.37 grams, 23 mmol) in tetrahydrofuran (30 ml) at −78° C. under a nitrogen atmosphere. After 1 hour a solution of benzyl 1-cyclohexene-1-carboxylate (5 grams, 23 mmol) in tetrahydrofuran (10 ml) was added by cannula and the reaction mixture was allowed to warm to room temperature over 12 hours. The reaction was quenched with saturated sodium chloride solution and diluted with ethyl acetate. The organic layer was separated, dried (sodium sulfate) and concentrated. The crude mixture was purified by silica gel chromatography (elution with 95% hexane/5% ethyl acetate) to provide benzyl-2-(4-bromobenzenethio)-1-cyclohexane-1-carboxylate.

Osmium tetroxide (1.53 ml of a 2.5% solution in 2-methyl-2-propanol) was added to a stirred solution of benzyl-2-(4-bromobenzenethio)-1-cyclohexane-1-carboxylate (3.1 grams, 7.65 mmol) and 4-methylmorpholine N-oxide (2.24 grams, 19 mmol) in aqueous acetone (15 ml water/30 ml acetone) at room temperature. After 12 hours the solvent was removed in vacuo and the residue was partitioned between dilute hydrochloric acid and ethyl acetate. The ethyl acetate layer was washed with brine, dried (sodium sulfate) and concentrated. The crude mixture was purified by silica gel chromatography (elution with dichloromethane) to provide benzyl-2-(4-bromobenzenesulfonyl)-1-cyclohexane-1-carboxylate.

Tetrakis-(triphenylphoshine)palladium (65 mg, 0.057 mmol) was added to a stirred solution of 2-methoxypyridyl-5-boronic acid (460 mg, 2.4 mmol) and benzyl-2-(4-bromobenzenesulfonyl)-1-cyclohexane-1-carboxylate (712 mg, 1.6 mmol) in a mixture of toluene (9 ml), ethanol (5 ml) and saturated sodium bicarbonate solution (4 ml). The mixture was refluxed for 3 hours after which time the organic solvent was removed by evaporation. The residue was extracted with ethyl acetate and the organics were washed with water and saturated sodium chloride solution. The organics were dried (sodium sulfate) and concentrated. The crude mixture was purified by silica gel chromatography (elution with 99% dichloromethane/1% methanol) to provide benzyl-2-(4-(2-methoxy-5-pyridyl)-benzenesulfonyl)-1-cyclohexane-1-carboxylate.

Benzyl-2-(4-(2-methoxy-5-pyridyl)-benzenesulfonyl)-1-cyclohexane-1-carboxylate (230 mg, 0.49 mmol) was dissolved in 20 ml ethanol. 10% Palladium on carbon (30 mg) was added and the reaction mixture was heated at 60° C. under a pressure of 50psi hydrogen for 12 hours. The mixture was cooled, the catalyst removed by filtration and the solvent concentrated. The crude mixture was purified by silica gel chromatography (elution with 95% dichloromethane/5% methanol) to provide 2-(4-(5-(2-methoxypyridyl) -benzenesulfonyl)-1-cyclohexane-1-carboxylate.

1-Hydroxybenztriazole (80 mg, 0.6 mmol) and 1-(3-dimethylaminopropyl)-3-ethylcarbodiimide (143 mg, 0.7 mmol) were added to a stirred solution of 2-(4-(2-methoxy-5-pyridyl)-benzenesulfonyl)-1-cyclohexane-1-carboxylate (200 mg, 0.5 mmol) in dichloromethane (8 ml) at room temperature. After 30 minutes tert-butyldimethylsilyhydroxylamine (157 mg, 1 mmol) and 4-methylmorpholine (0.14 ml, 1 mmol) were added and the mixture was stirred for 12 hours. The solvent was removed and the reaction mixture was stirred for 2 hours in methanol/water (10 ml/4 ml). The reaction mixture was concentrated and the crude mixture was purified by silica gel chromatography (elution with 98% dichloromethane/2% methanol) to provide N-hydroxy-2-(4-(2-methoxy-5-pyridyl)) benzenesulfonyl)-cyclohexane-1-carboxamideMass spectrum (thermospray): m/Z 391 (MH$^+$), 408 (MNH$_4^+$). $^1$H NMR (CDCl$_3$, 400 MHz, ppm) δ8.40 (s, 1H), 7.90 (d, 2H), 7.80 (d, 1 H), 7.65 (d, 2H), 6.80 (d, 1 H), 4.00 (s, 3H), 3.20 (m, 1H), 3.05 (m, 1H), 2.30–1.20 (m, 8H).

EXAMPLE 8

N-Hydroxy-2-(4-bromobenzenesulfoxy)-cyclohexane-1-carboxamide

N-Butyl lithium (2.86 ml of a 2.5M solution in hexanes) was added to a stirred solution of 4-bromothiophenol (14.8 grams, 78.5 mmol) in (300 ml) at −78° C. under a nitrogen atmosphere. After 1 hour a solution of methyl 1-cyclohexene-1-carboxylate (10 grams, 71.4 mmol) in tetrahydrofuran (20 ml) was added by cannula and the reaction mixture was allowed to warm to room temperature over 12 hours. The reaction was quenched with saturated sodium chloride solution and diluted with ethyl acetate. The organic layer was separated, dried (sodium sulfate) and concentrated. The crude mixture was dissolved in dioxane (250 ml) and water (80 ml) and 2M sodium hydroxide solution (100 ml) was added. The mixture was stirred for 12 hours and then the pH was adjusted to pH 1–3 with concentrated hydrochloric acid. The dioxane was removed by evaporation and the product was extracted into dichloromethane. The organic layer was dried (sodium sulfate) and concentrated. The crude mixture was purified by silica gel chromatography (elution with 30% ethyl acetate/70% hexane) to provide 2-(4-bromobenzenethio)-1-cyclohexane-1-carboxylate (contaminated with cyclohexene-1-carboxylate).

1-Hydroxybenztriazole (1.9 grams, 14 mmol) and 1-(3-dimethylaminopropyl)-3-ethylcarbodiimide (2.69 grams, 14 mmol) were added to a stirred solution of 2-(4-bromobenzenethio)-1-cyclohexane-1-carboxylate (3.69 grams, 11.6 mmol) in imethylformamide (50 ml) at room temperature. After 30 minutes hydroxylamine hydrochloride (3.25 grams, 47 mmol) and triethylamine (9.7 ml, 70 mmol) were added nd the mixture was stirred for 12 hours. The solvent was removed and the reaction mixture was extracted from water with ethyl acetate. The organics were concentrated and the crude mixture was purified by silica gel chromatograph (elution with 98% dichloromethane/2% methanol) to provide N-hydroxy-2-(4-bromobenzenethio)-cyclohexane-1-carboxamide. m–Chloroperbenzoic acid (273 mg, 0.8 mmol of 50% pure solid) was added to a stirred solution of N-hydroxy-2-(4-bromobenzenethio)-cyclohexane-1-carboxamide (290 mg, 0.88 mmol) in dichloromethane (5 ml) at 0° C. After 2 hours the mixture was diluted with further dichloromethane and washed with brine. The organic layer was dried (sodium sulfate) and concentrated. The crude mixture was purified by silica gel chromatography (elution with 98% dichloromethane/2% methanol) to provide N-hydroxy-2-(4- bromobenzenesulfoxy)-cyclohexane-1-carboxamide. Mass spectrum (thermospray): m/Z 346 (MH⁺). ¹H NMR (CDCl₃, 400 MHz, ppm) δ10.50 (br s, 1H), 7.70 (d, 2H), 7.55 (d, 2H), 2.95 (m, 1H), 2.80 (m, 1H), 2.20–2.00 (m, 2H), 1.90–1.10 (m, 6H).

EXAMPLE 9

N-hydroxy-2-(4-methoxybenzenesulfoxy)-cyclohexane-1-carboxamide

The title compound of Example 9 was prepared by a method analogous to that described in Example 8.

Mass spectrum (thermospray): m/Z 298.0 (MH⁺). ¹H NMR (CDCl₃, 400 MHz, ppm) δ 7.60 (d, 2H), 7.10 (d, 2H), 3.90 (s, 3H), 3.00 (m, 1 H), 2.90 (m, 1 H), 2.25 (m, 1 H), 2.10–1.40 (m, 7H).

We claim:

1. A compound of the formula

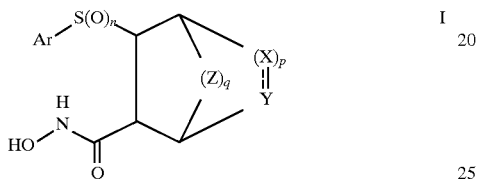

or a pharmaceutically acceptable salt thereof, wherein the broken line represents an optional double bond;

n is 0,1 or 2;

p is 0 or 1;

q is 0, 1 or 2;

X, Y and Z are each independently $CR^1R^2$ wherein $R^1$ and $R^2$ are each independently hydrogen, $(C_1-C_6)$alkyl optionally substituted by $(C_1-C_6)$alkylamino, $(C_1-C_6)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_6-C_{10})$aryl$(C_6-C_{10})$aryl, $(C_3-C_6)$cycloalkyl, hydroxy$(C_1-C_6)$alkyl, $(C_1-C_6)$alkyl (hydroxymethylene), piperazinyl, $(C_6-C_{10})$aryl $(C_1-C_6)$alkoxy, $(C_5-C_9)$heteroaryl$(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amine; $(C_2-C_6)$alkenyl, $(C_6-C_{10})$aryl$(C_2-C_6)$alkenyl, $(C_5-C_9)$heteroaryl $(C_2-C_6)$alkenyl, $(C_2-C_6)$alkynyl, $(C_6-C_{10})$aryl$(C_2-C_6)$ alkynyl, $(C_5-C_9)$heteroaryl$(C_2-C_6)$alkynyl, $(C_1-C_6)$ alkylamino, $(C_1-C_6)$alkylthio, $(C_1-C_6)$alkoxy, trifluoromethyl, $(C_1-C_6)$alkyl (difluoromethylene), $(C_1-C_3)$alkyl(difluoromethylene)$(C_1-C_3)$alkyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$ heteroarylamino, $(C_5-C_9)$heteroarylthio, $(C_5-C_9)$ heteroaryloxy, $(C_3-C_6)$cycloalkyl, $(C_1-C_6)$alkyl (hydroxymethylene), piperidyl, $(C_1-C_6)$alkylpiperidyl, $(C_1-C_6)$acylamino, $(C_1-C_6)$acylthio, $(C_1-C_6)$acyloxy, $R^3(C_1-C_6)$alkyl wherein $R^3$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl $(C_1-C_6)$ alkylpiperazino, $(C_5-C_9)$heteroaryl$(C_1-C_6)$ alkylpiperazino, morpholino, thiomorpholino, piperidino, pyrrolidino, piperidyl, $(C_1-C_6)$ alkylpiperidyl, $(C_6-C_{10})$arylpiperidyl, $(C_{51}-C_9)$ heteroarylpiperidyl, $(C_1-C_6)$alkylpiperidyl$(C_1-C_6)$ alkyl, $(C_6-C_{10})$arylpiperidyl$(C_1-C_6)$alkyl, $(C_5-C_9)$ heteroarylpiperidyl$(C_1-C_6)$alkyl, or $(C_1-C_6)$ acylpiperidyl; or a group of the formula

wherein r is 0 to 6;

D is hydroxy, $(C_1-C_6)$alkoxy or $NR^4R^5$ wherein $R^4$ and $R^5$ are each independently selected from the group consisting of hydrogen, $(C_1-C_6)$alkyl optionally substituted by $(C_1-C_6)$alkylpiperidyl, $(C_6-C_{10})$ arylpiperidyl, $(C_5-C_9)$heteroarylpiperidyl, $(C_6-C_{10})$ aryl, $(C_5-C_9)$heteroaryl, $(C_6-C_{10})$aryl$(C_6-C_{10})$aryl or $(C_3-C_6)$cycloalky; piperidyl, $(C_1-C_6)$alkylpiperidyl, $(C_6-C_{10})$arylpiperidyl, $(C_5-C_9)$heteroarylpiperidyl, $(C_1-C_6)$acylpiperidyl, $(C_6-C_{10})$aryl, $(C_5-C_9)$ heteroaryl, $(C_6-C_{10})$aryl$(C_6-C_{10})$aryl, $(C_3-C_6)$ cycloalkyl, $R^6(C_2-C_6)$alkyl, $(C_1-C_5)$alkyl(CHR⁶) $(C_1-C_6)$alkyl wherein $R^6$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$ alkylsulfinyl, $(C_6-C_{10})$arylsulfinyl, $(C_1-C_6)$ alkylsulfoxyl, $(C_6-C_{10})$arylsulfoxyl, amino, $(C_1-C_6)$ alkylamino, $((C_1-C_6)$alkyl$)_2$amino, $(C_1-C_6)$ acylpiperazino, $(C_1-C_6)$alkylpiperazino, $(C_6-C_{10})$aryl $(C_1-C_6)$alkylpiperazino, $(C_5-C_{10})$heteroaryl$(C_1-C_6)$ alkylpiperazino, morpholino, thiomorpholino, piperidino or pyrrolidino; $R^7(C_1-C_6)$alkyl, $(C_1-C_5)$ alkyl(CHR⁷)$(C_1-C_6)$alkyl wherein $R^7$ is piperidyl or $(C_1-C_6)$alkylpiperidyl; and CH(R⁸)COR⁹ wherein $R^8$ is hydrogen, $(C_1-C_6)$alkyl, $(C_6-C_{10})$aryl$(C_1-C_6)$alkyl, $(C_5-C_9)$heteroaryl$(C_1-C_6)$alkyl, $(C_1-C_6)$alkylthio $(C_1-C_6)$alkyl, $(C_6-C_{10})$arylthio$(C_1-C_6)$alkyl, $(C_1-C_6)$ alkylsulfinyl$(C_1-C_6)$alkyl, $(C_6-C_{10})$arylsulfinyl $(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(C_1-C_6)$ alkyl, amino$(C_1-C_6)$alkyl, $(C_1-C_6)$alkylamino$(C_1-C_6)$ alkyl, $((C_1-C_6)$alkylamino$)_2(C_1-C_6)$alkyl, $R^{10}R^{11}NCO$ $(C_1-C_6)$alkyl or $R^{10}OCO(C_1-C_6)$alkyl wherein $R^{10}$ and $R^{11}$ are each independently selected from the group consisting of hydrogen, $(C_1-C_6)$alkyl, $(C_6-C_{10})$aryl $(C_1-C_6)$alkyl and $(C_5-C_9)$heteroaryl$(C_1-C_6)$alkyl; and $R^9$ is $R^{12}O$ or $R^{12}R^{13}N$ wherein $R^{12}$ and $R^{13}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl; and Ar is $(C_6-C_{10})$aryl or $(C_5-C_9)$heteroaryl, each of which may be optionally substituted by $(C_6-C_{10})$aryl, $(C_5-C_9)$ heteroaryl, $(C_6-C_{10})$aryl$(C_2-C_6)$alkenyl, $(C_5-C_9)$ heteroaryl$(C_2-C_6)$alkenyl,$(C_2-C_6)$alkynyl, $(C_6-C_{10})$ aryl$(C_2-C_6)$alkynyl or $(C_5-C_9)$heteroaryl$(C_2-C_6)$ alkynyl optionally substituted by $(C_1-C_6)$alkyl, $(C_1-C_6)$alkylamino, $(C_1-C_6)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$ aryloxy, $(C_5-C_9)$heteroarylamino, $(C_5-C_9)$ heteroarylthio, $(C_5-C_9)$heteroaryloxy, $(C_6-C_{10})$aryl $(C_6-C_{,10})$aryl, $(C_3-C_6)$cycloalkyl, hydroxy$(C_1-C_6)$ alkyl, $(C_1-C_6)$alkyl(hydroxymethylene), piperazinyl, $(C_6-C_{10})$aryl$(C_6-C_{10})$alkoxy, $(C_5-C_9)$heteroaryl $(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$ arylsulfinyl, $(C_1-C_6)$alkylsulfonyl, $(C_6-C_{10})$ arylsulfonyl, amino, $(C_1-C_6)$alkylamino, $((C_1-C_6)$ alkyl$)_2$amino or $R^3$alkyl wherein $R^3$ is defined as above; halo, hydroxy, $(C_1-C_6)$alkyl or $(C_1-C_6)$alkoxy wherein the alkyl or alkoxy groups may be optionally substituted by $(C_1-C_6)$alkylamino, $(C_1-C_6)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_6-C_{10})$aryl $(C_6-C_{10})$aryl, $(C_3-C_6)$cycloalkyl, hydroxy$(C_1-C_6)$alkyl, $(C_1-C_6)$alkyl(hydroxymethylene), piperazinyl, $(C_6-C_{10})$aryl$(C_1-C_6)$alkoxy, $(C_5-C_9)$heteroaryl $(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amino; $(C_2-C_6)$alkenyl, $(C_6-C_{10})$aryl$(C_2-C_6)$alkenyl, $(C_5-C_9)$heteroaryl$(C_2-C_6)$alkenyl, $(C_2-C_6)$alkynyl, $(C_6-C_{10})$aryl$(C_2-C_6)$alkynyl, $(C_5-C_9)$heteroaryl$(C_2-C_6)$alkynyl, $(C_1-C_6)$alkylamino, $(C_1-C_6)$alkylthio, $(C_1-C_6)$alkoxy, trifluoromethyl, $(C_1-C_6)$alkyl (difluoromethylene), $(C_1-C_3)$alkyl (difluoromethylene)$(C_1-C_3)$alkyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_3-C_6)$cycloalkyl, $(C_1-C_6)$alkyl(hydroxymethylene), piperidyl, $(C_1-C_6)$alkylpiperidyl, $(C_1-C_6)$acylamino, $(C_1-C_6)$acylthio, $(C_1-C_6)$acyloxy, $R^3(C_1-C_6)$alkyl or $R^3(C_1-C_6)$alkoxy wherein $R^3$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_1-C_6)$alkylpiperidyl$(C_1-C_6)$alkyl, $(C_6-C_{10})$arylpiperidyl$(C_1-C_6)$alkyl, $(C_5-C_9)$heteroarylpiperidyl$(C_1-C_6)$alkyl, $(C_1-C_6)$acylpiperidyl, or a group of the formula

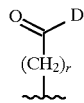

wherein r and D are as defined above;

with the proviso that when q is 1 and X and Y are both $CR^1R^2$ wherein one of either $R^1$ or $R^2$ must be hydrogen, p must be 1;

with the proviso that when q is 0, the compound of formula I is not bicyclic; and with the proviso that when the broken line of formula I represents a double bond, $R^2$ does not exist.

2. A compound according to claim 1, wherein q is 0 or 2.

3. A compound according to claim 1, wherein q is 0 or 1.

4. A compound according to claim 1, wherein n is 2.

5. A compound according to claim 1, wherein X and Y are both $CR^1R^2$ wherein $R^1$ and $R^2$ are hydrogen.

6. A compound according to claim 1, wherein Ar is methoxyphenyl, phenoxyphenyl, benzoxyphenyl or halophenyl.

7. A compound according to claim 1, wherein q is 0, p is 1, n is 2, X and Y are each $CR^1R^2$ each of $R^1$ and $R^2$ is hydrogen and Ar is methoxyphenyl, phenoxyphenyl or benzoxyphenyl.

8. A compound according to claim 1, wherein q is 0, p is 0, m is 2, X and Y are each $CR^1R^2$ each of $R^1$ and $R^2$ is hydrogen and Ar is methoxyphenyl, phenoxyphenyl or benzoxyphenyl.

9. A pharmaceutical composition for (a) the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of claim 1 or a pharmaceutically acceptable salt thereof, effective in such treatments and a pharmaceutically acceptable carrier.

10. A method for the inhibition of (a) matrix metalloproteinases or (b) the production of tumor necrosis factor (TNF) in a mammal, including a human, comprising administering to said mammal an effective amount of a compound of claim 1 or a pharmaceutically acceptable salt thereof.

11. A method for treating a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor (TNF) in a mammal, including a human, comprising administering to said mammal an amount of a compound of claim 1 or a pharmaceutically acceptable salt thereof, effective in treating such a condition.

* * * * *